(12) United States Patent
Anderson

(10) Patent No.: US 10,945,545 B2
(45) Date of Patent: Mar. 16, 2021

(54) WHOLE-HEAD PILLOW

(71) Applicant: Thomas Anderson, Arlington, VA (US)

(72) Inventor: Thomas Anderson, Arlington, VA (US)

( * ) Notice: Subject to any disclaimer, the term of this patent is extended or adjusted under 35 U.S.C. 154(b) by 219 days.

(21) Appl. No.: 16/272,078

(22) Filed: Feb. 11, 2019

(65) Prior Publication Data

US 2020/0253396 A1 Aug. 13, 2020

(51) Int. Cl.
*A47G 9/10* (2006.01)
*A61F 9/04* (2006.01)

(52) U.S. Cl.
CPC ........... *A47G 9/109* (2013.01); *A47G 9/1081* (2013.01); *A61F 9/04* (2013.01); *A61F 9/045* (2013.01); *A47G 2009/1018* (2013.01)

(58) Field of Classification Search
CPC .................. A61G 13/121; A47G 9/109; A47G 2009/1018; A47G 9/1045; A61F 9/045; A47C 7/383; A42B 3/069; A42B 3/10; A42B 3/064; F41H 1/04; A41D 2200/20
See application file for complete search history.

(56) References Cited

U.S. PATENT DOCUMENTS

| | | | | |
|---|---|---|---|---|
| 4,679,263 A | * | 7/1987 | Honer | A47C 7/383 297/393 |
| 6,651,256 B1 | * | 11/2003 | Swift | A42B 1/004 2/15 |
| 9,381,106 B2 | * | 7/2016 | Gilmer | A61F 5/0102 |
| 2013/0046219 A1 | * | 2/2013 | Mendez | A61F 13/12 602/17 |

* cited by examiner

*Primary Examiner* — David R Hare
*Assistant Examiner* — Madison Emanski
(74) *Attorney, Agent, or Firm* — Maskell Law PLLC; Benjamin E. Maskell

(57) ABSTRACT

Disclosed is a pillow having a head portion having a head-shaped cavity sized in approximate proportions to receive a human head. The head portion has an inner surface, an outer surface, an open face, a left side, a left-side ear hole, a right side, a right-side ear hole, and an open bottom. There are a plurality of pads inside the head-shaped cavity that are selectively removable from the head-shaped cavity to accommodate a variety of head sizes and a washable liner covering the plurality of pads that is selectively removable from the pillow to accommodate laundering. The pillow has a neck portion extending from the open bottom and a circumferential pad on the outer surface of the head portion that is selectively removable to increase or decrease the size of the head portion.

19 Claims, 8 Drawing Sheets

WHOLE-HEAD PILLOW

BACKGROUND OF THE INVENTION

Field of the Invention

The embodiments of the invention relate pillows, and more particularly, to a pillow for use while sleeping. Although embodiments of the invention are suitable for a wide scope of applications, it is particularly suitable for those who move frequently while sleeping.

Discussion of the Related Art

Pillows for sleeping are commonly used to provide cushioning and support for the head and neck. Traditional pillows of the related art are generally rectangular sacks filled with a cushioning material such as goose down, duck feathers, or polyester batting. Non-traditional pillows of the related art are also generally rectangular, but may be formed from foam or other materials and have varying contours to support the head and neck.

The related art pillows, however, have many deficiencies. For example, related art pillows are commonly placed on the sleeping surface and a user would place their head on top of the pillow. If the user were to roll over during sleep, however, the user may roll off the pillow and experience cramping, discomfort, or be awoken. The user may have to reposition or fluff the pillow during the night thereby disrupting restful sleep. Pillows of the related are commonly of a single size—that is the pillow cannot be configured for thickness or firmness according to user preference. Users, however, have varying body dimensions and preferences and a pillow having static dimensions can be unsuitable for some users. In the related art, pillows can be stacked or layered to accommodate some user preference, but pillows, by their nature are subject to compression and movement and are not well suited to stacking. Accordingly, there is a need for a pillow that solves the problems of the related art by providing a pillow that accommodates "active sleepers" having varying pillow preferences.

SUMMARY OF THE INVENTION

Accordingly, embodiments of the invention are directed to a whole-head pillow that substantially obviates one or more of the problems due to limitations and disadvantages of the related art.

An object of embodiments of the invention is to provide a pillow suited for "active sleepers" that move frequently during the night.

Another object of embodiments of the invention is to provide a pillow that is easily customizable in accordance with user preference.

Yet another object of embodiments of the invention is to facilitate restful sleep.

Still another object of embodiments of the invention is to obviate the need to adjust, fluff, and reposition a pillow during the night.

Additional features and advantages of embodiments of the invention will be set forth in the description which follows, and in part will be apparent from the description, or may be learned by practice of embodiments of the invention. The objectives and other advantages of the embodiments of the invention will be realized and attained by the structure particularly pointed out in the written description and claims hereof as well as the appended drawings.

To achieve these and other advantages and in accordance with the purpose of embodiments of the invention, as embodied and broadly described, a whole-head pillow includes a head portion having a head-shaped cavity sized in approximate proportions to receive a human head. The head portion has an inner surface, an outer surface, an open face, a left side, a left-side ear hole, a right side, a right-side ear hole, and an open bottom. There are a plurality of pads inside the head-shaped cavity that are selectively removable from the head-shaped cavity to accommodate a variety of head sizes and a washable liner covering the plurality of pads that is selectively removable from the pillow to accommodate laundering. The pillow has a neck portion extending from the open bottom and a circumferential pad on the outer surface of the head portion that is selectively removable to increase or decrease the size of the head portion.

In another aspect, a whole-head pillow includes a pillow selectively securable to a user's head including a head receiving portion, the head receiving portion sized in approximate proportions to receive a human head and comprising, a rear wall, a first sidewall, a first ear-hole in the first sidewall, a second sidewall, a second ear-hole in the second sidewall, an open front, an open bottom, a strap having a first end fixed to the first sidewall, a strap receiving portion fixed to the second sidewall, the strap receiving portion configured to receive the strap, a first pad selectively attached to an inside surface of the head receiving portion for sizing the head receiving portion in accordance with user preference, and a second pad selectively attached to an outside surface of the head receiving portion for sizing the head receiving portion in accordance with user preference.

In yet another aspect, a whole-head pillow includes an orthopedic pillow to be secured to a user's head during sleep, the orthopedic pillow including a contoured socket for receiving the user's head, the contoured socket and configured to substantially cover a back and sides of the user's head, a front opening of the contoured socket, a strap fixed to a first side of the front opening and configured to interface with an attachment point on a second side of the front opening, the strap and the attachment point configured to cooperate to secure the user's head in the contoured socket, a first pad removably attached to an inside surface of the contoured socket to adjust the size of the contoured socket, a second pad removably attached to an outside surface of the contoured socket, and a removable liner covering at least part of the inside surface of the of the contoured socket.

It is to be understood that both the foregoing general description and the following detailed description are exemplary and explanatory and are intended to provide further explanation of embodiments of the invention as claimed.

BRIEF DESCRIPTION OF THE DRAWINGS

The accompanying drawings, which are included to provide a further understanding of embodiments of the invention and are incorporated in and constitute a part of this specification, illustrate embodiments of the invention and together with the description serve to explain the principles of embodiments of the invention.

DETAILED DESCRIPTION OF THE PREFERRED EMBODIMENTS

Figure 1:
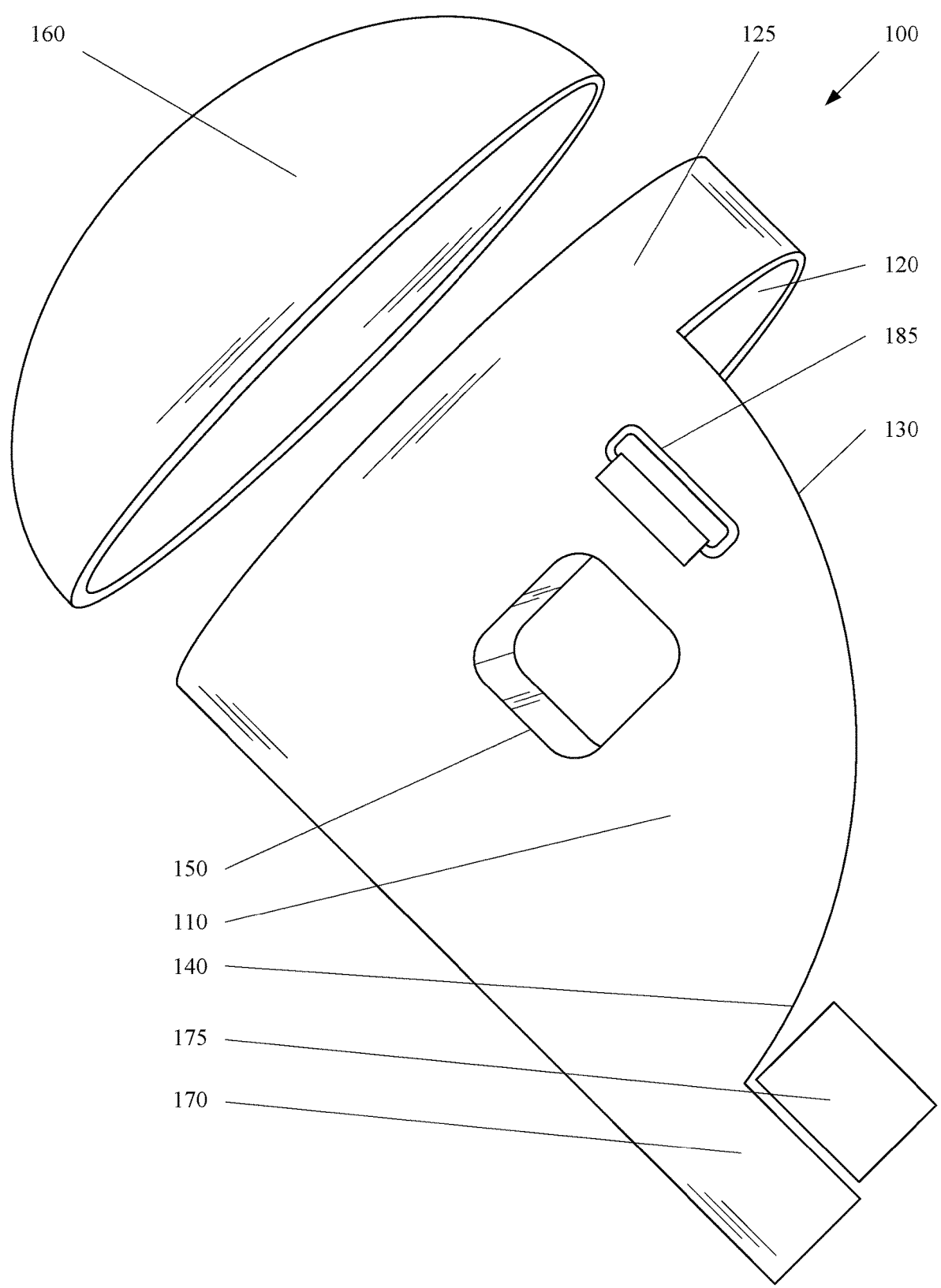
FIG. 1 is an isometric view of a right-side of a whole-head pillow according to an exemplary embodiment of the invention.

Reference will now be made in detail to the preferred embodiments of the invention, examples of which are illustrated in the accompanying drawings. The invention may, however, be embodied in many different forms and should not be construed as being limited to the embodiments set forth herein; rather, these embodiments are provided so that this disclosure will be thorough and complete, and will fully convey the concept of the invention to those skilled in the art. In the drawings, the thicknesses of layers and regions are exaggerated for clarity. Like reference numerals in the drawings denote like elements.

The herein described embodiments of a whole-head pillow make relative reference to various parts thereof. For clarity, embodiments of the whole-head pillow are intended to be worn on a user's head like a helmet. Relative references, such as "the left side" and "the right side", refer to the left (or right) of the pillow from the point of view of a person using the pillow. "Top" refers to the portions near a top of a user's head. "Front" or "face" refer to portions near a user's face. "Bottom" or "neck" refer to lower portions of the pillow near a user's neck and shoulders. "Back" refers to the back of the pillow near a back of the user's head. "Inside" and "inside surface(s)" refer to the inside of the pillow adjacent a user's head. "Outside" and "outside surface(s)" refer to the externally facing portions of the pillow.

This application makes references to portions of the invention that are "selectively removable", "selectively attached", "removable", and "removably attached." These terms mean that the specified components are non-permanently attached in such a way that they can be easily separated without damaging the pillow and subsequently reattached with relative ease. Such methods of attachment include hook-and-loop fasteners (Velcro), buttons, latches, hooks, ties, buckles, straps, magnets, and the like. While preferred embodiments of the invention disclosed herein show and describe hook-and-loop fasteners, the aforementioned terms are not intended to be limited to just hook-and-loop fasteners and are used in their broadest sense to include all manner of attachments commonly used to non-permanent join textiles.

The term "Velcro" is through this specification in the generic sense and intended to refer generally to hook-and-loop fastener. Although Velcro comprises a strip of hook material and a mating strip of loop material, references to Velcro mean either the combination, or individually a hook strip or a loop strip as may appropriate to mate with the corresponding strip.

Figure 2:
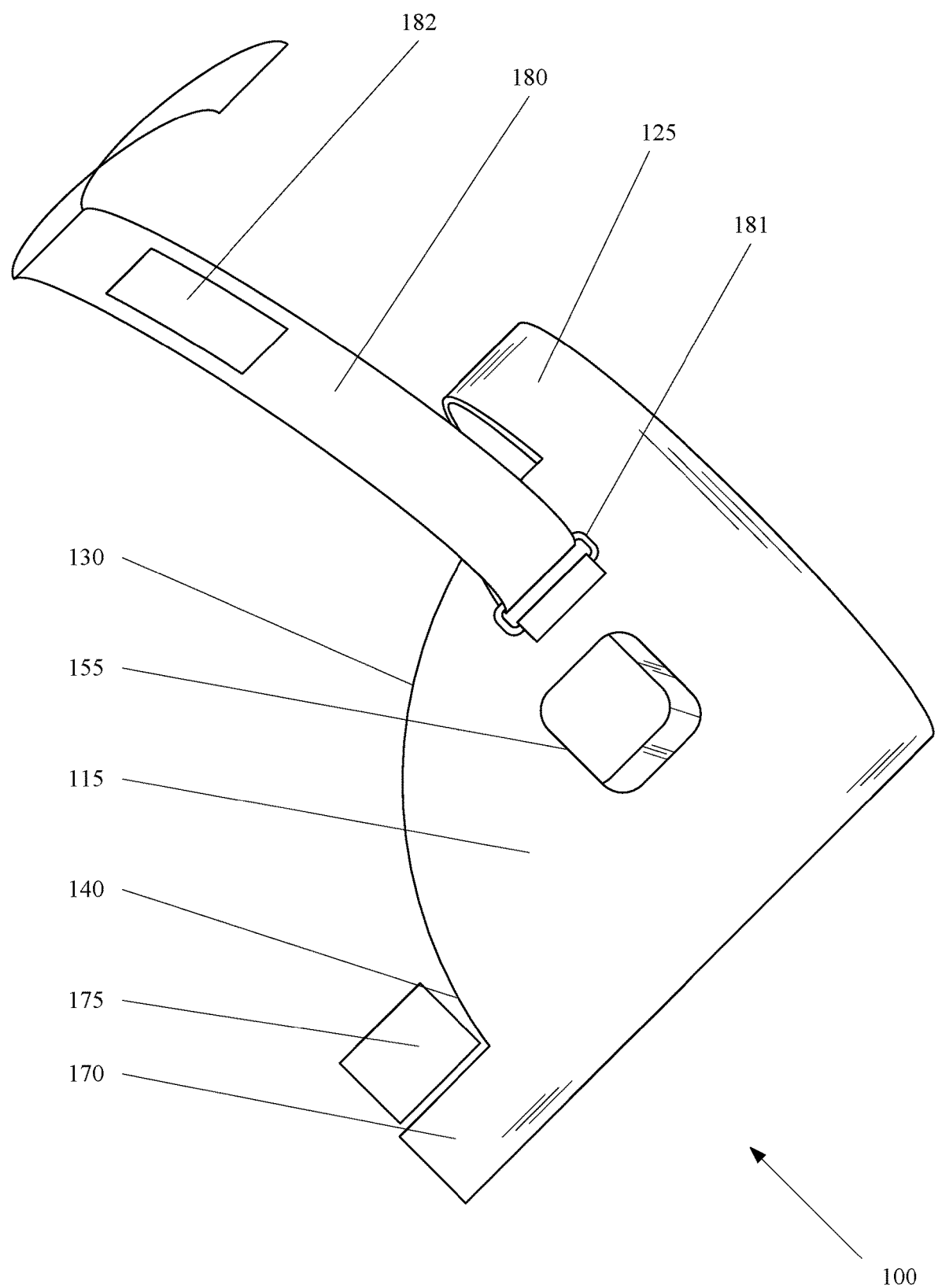
FIG. 2 is an isometric view of a left-side of a whole-head pillow according to an exemplary embodiment of the invention.

FIG. 1 is an isometric view of a right-side of a whole-head pillow according to an exemplary embodiment of the invention and FIG. 2 is an isometric view of a left-side of a whole-head pillow according to an exemplary embodiment of the invention. As shown in FIG. 1 and FIG. 2, a whole-head pillow 100 includes a right side 110, a left side 115, an inside surface 120, an outside surface 125, an open face 130, and open bottom 140, a right earhole 150, a left earhole 155, a top 160, a neck portion 170, a neck pad 175, and a strap 180. The strap 180 has an anchor point 181, a Velcro pad 182, and an attachment point 185. The strap 180 can have a second Velcro pad (not shown) to mate with Velcro pad 182.

The pillow 100 has a generally cylindrical body formed by the left side 115 and right side 110 with an open top, open face 130, and open bottom 140. The left side 115 and right side 110 can form a hollow cavity or contoured socket in the pillow for receiving a user's head. The inside surface 120 of the cavity of the pillow can be shaped in approximate proportions to accommodate a human head. Removable pads (not shown) can be provided to size the pillow in accordance with user preference.

The left side 115 can have an earhole 155 and right side 110 can have an earhole 150. The earholes 150 and 155 can serve a dual purpose to allow a user to hear sounds (such as an alarm clock) and also to provide for airflow to prevent the user from overheating.

The top portion of the pillow 100 can be open and, when worn, a user's head can protrude therefrom. An open top can provide ventilation for user comfort. A top 160 can be provided that matches the relative dimensions of the top of the pillow 100 and can be removably attached to the pillow 100 in accordance with user preference.

The neck portion 170 can extend downward from the open bottom 140. The neck portion can have a removable pad 175 that can support a user's neck. The pad 175 can be selected in accordance with user preference for size and firmness.

A strap 180 can secure a user's head in the pillow 100. The strap 180 can be permanently fixed at anchor point 181 on the left side 115 of the pillow 100. The strap 180 can be attached the right side 110 to attachment point 185. The strap 180 can have a Velcro pad 182 which can mate with a second Velcro pad (not shown) on the strap 180 to removably secure the strap.

A user can don the pillow 100 by sliding the pillow down over the head so that the user's face is positioned by the open face 130 of the pillow 100 and the user's ears are positioned near earholes 150 and 155. A user can secure the pillow by threading the free end of the strap 180 through the attachment point 185, doubling the strap 180 back upon itself, and securing it on the Velcro pad 182. Once attached, the whole-head pillow 100 is not reasonably susceptible to movement so, as a user repositions their body throughout a night of sleep, the user does not have to also reposition and re-fluff the pillow. This can contribute to more restful sleep.

The structures of the whole head pillow can be made from materials that are commonly known in the art. For example, the main structure of the whole head pillow 100 can be made from memory foam. The structure can be covered in a natural or synthetic cloth such as cotton, nylon, or polyester for comfort and breathability. The structure can optionally include stiffening portions such as high density foam to maintain the shape and structure of the pillow. In preferred embodiments of the invention, high density foam can be sandwiched between layers of memory foam to achieve a soft, yet semi-rigid structure. Layers of foam can be secured with glue or stitching. Fabric covers for the foam can be secured with glue or stitching.

Figure 3:
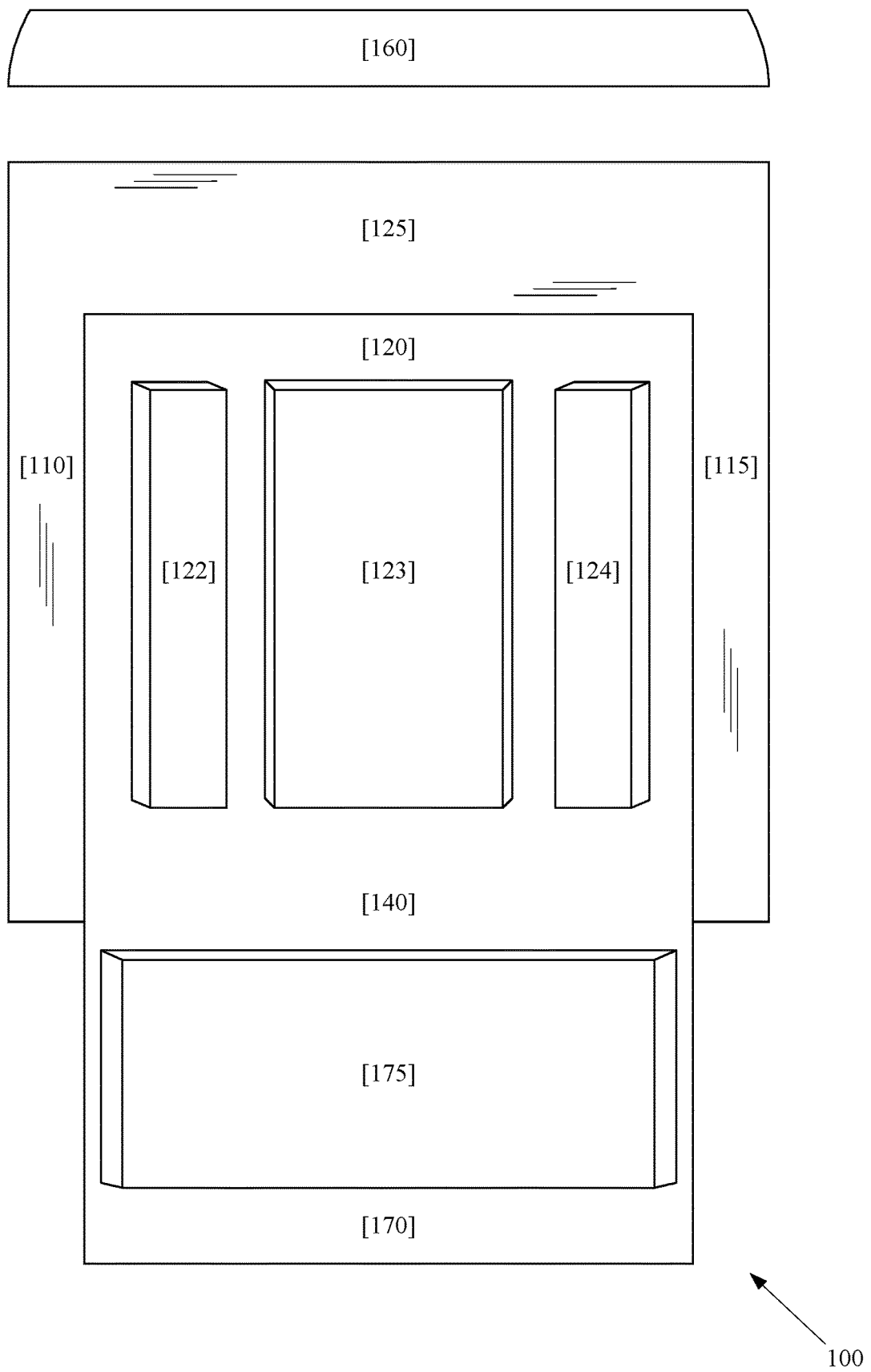
FIG. 3 is a front view of a whole-head pillow according to an exemplary embodiment of the invention.

FIG. 3 is a front view of a whole-head pillow according to an exemplary embodiment of the invention. As shown in FIG. 3, a whole-head pillow 100 can have a right side 110, a left side 115, an inside surface 120, an outside surface 125, an open bottom 140, a removable top 160, a next portion 170, and a removable neck pad 175. The inside surface can have a plurality of pads 122, 123, and 124.

The whole-head pillow 100 can be worn on a head of a user such that the left side 115 is adjacent a user's left ear and the right side 110 is adjacent a user's right ear. The user's next can extend through the open bottom 140 and cover the neck portion 170. The pad 175 can be removably attached to the neck portion 170 so that a user can swap and select a pad 175 having a size and firmness according to user preference.

The pads 122, 123, and 124 on the inside surface 120 can be selected to size the inside surface 120 to closely fit a user's head. The pads 122, 123, and 124 can be removably attached with Velcro so that the pads 122, 123, and 124 can be easily swapped and configured with other pads having varying thicknesses and firmness in accordance with user preference. Although the embodiment of FIG. 2 shows and describes three pads 122, 123, and 124 radially disposed on the inside surface 120, it is contemplated that varying configurations of pads can meet the objectives of the invention and such varied configurations are considered part of and within the scope of the invention. By way of non-limiting example, while three pads 122, 123, and 124 are shown, it is contemplated that the strap (180 in FIG. 2) will pull the left side 115 and the right side 110 together and it may be unnecessary to have pads 122 and 124. It is further contemplated that pads 122, 123, and 124 may be substituted with a single pad that is removably attached to the inside surface 120. While pads 122, 123, and 124 are shown in FIG. 3, it is contemplated there may be other pads in other locations on the inside surface 120 to shape, size, and generally conform the pillow in accordance with user head size and preference. There may be, for example, other pads near or inside the top 160 of the pillow 100 to size the top 160 to varying sizes of user heads.

The neck portion 170 can have a removable pad 175. The removable pad 175 can provide neck support to a user. The removable pad 175 can be swapped for other pads (not shown) so that a user can select a neck pad 175 having a thickness and firmness in accordance with user preference.

The top 160 can be removed from the pillow 100. It is contemplated that wearing the pillow 100 can cause a user to be hot and thus removing the top 160 can provide ventilation and cooling to a user. The top 160 can be removably attached to the body of the pillow 100.

Figure 4:
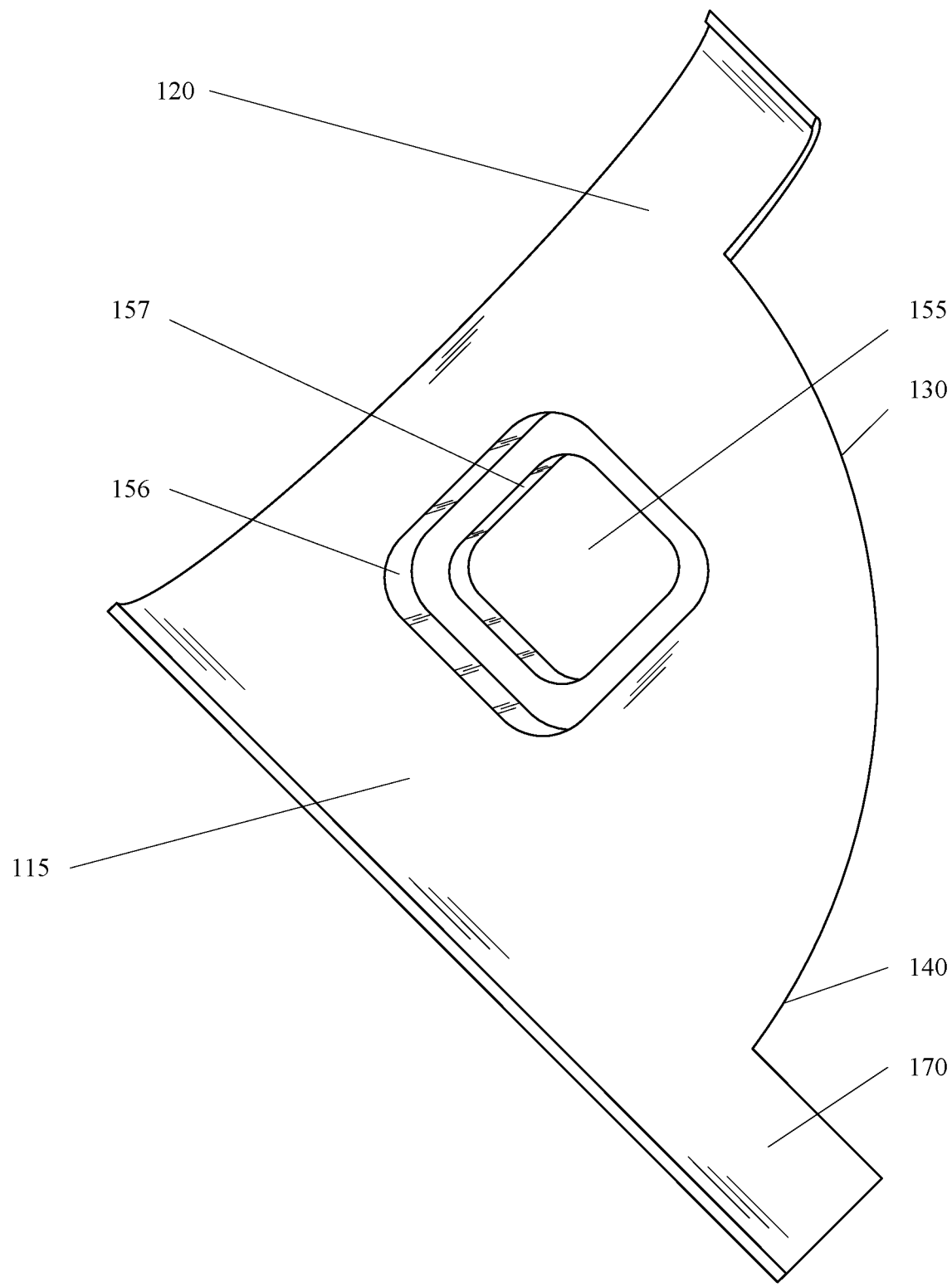
FIG. 4 is a cross-sectional view of a whole-head pillow according to an exemplary embodiment of the invention.

FIG. 4 is a cross-sectional view of a whole-head pillow according to an exemplary embodiment of the invention. As shown in FIG. 4 a whole-head pillow can have a left side 115, an inside surface 120, an open face 130, an open bottom 140, and a neck portion 170. The left side 115 can have an earhole 155 having an inner portion 156 and an outer portion 157.

The inner portion 156 of the earhole 155 can be large enough to accommodate a user's ear. It can be uncomfortable to having pressure on the ear for extended durations, thus, according to embodiments of the invention, an inner portion 156 of the earhole 155 is large enough to accommodate a user's ear without placing substantial pressure on it. Nevertheless, it can be desirable that the outside surface (not shown) of the pillow is as uniform as possible so that there is even support. Thus, embodiments of the invention contemplate that an outer portion 157 of the earhole 155 is smaller than the inner portion 156. The earhole, generally, can allow for ventilation and allow a user to hear sounds in the case of an emergency. The inner portion 156 has a perimeter measured around the inside of the inner portion 156 of the earhole 155. The outer portion 157 also has a perimeter measured around the inside of the outer portion 157 of the earhole 155. The inner portion 156 can be larger than the outer portion 157. The inner portion 156 can have a perimeter that is greater than the perimeter of the outer portion 157.

Figure 5:
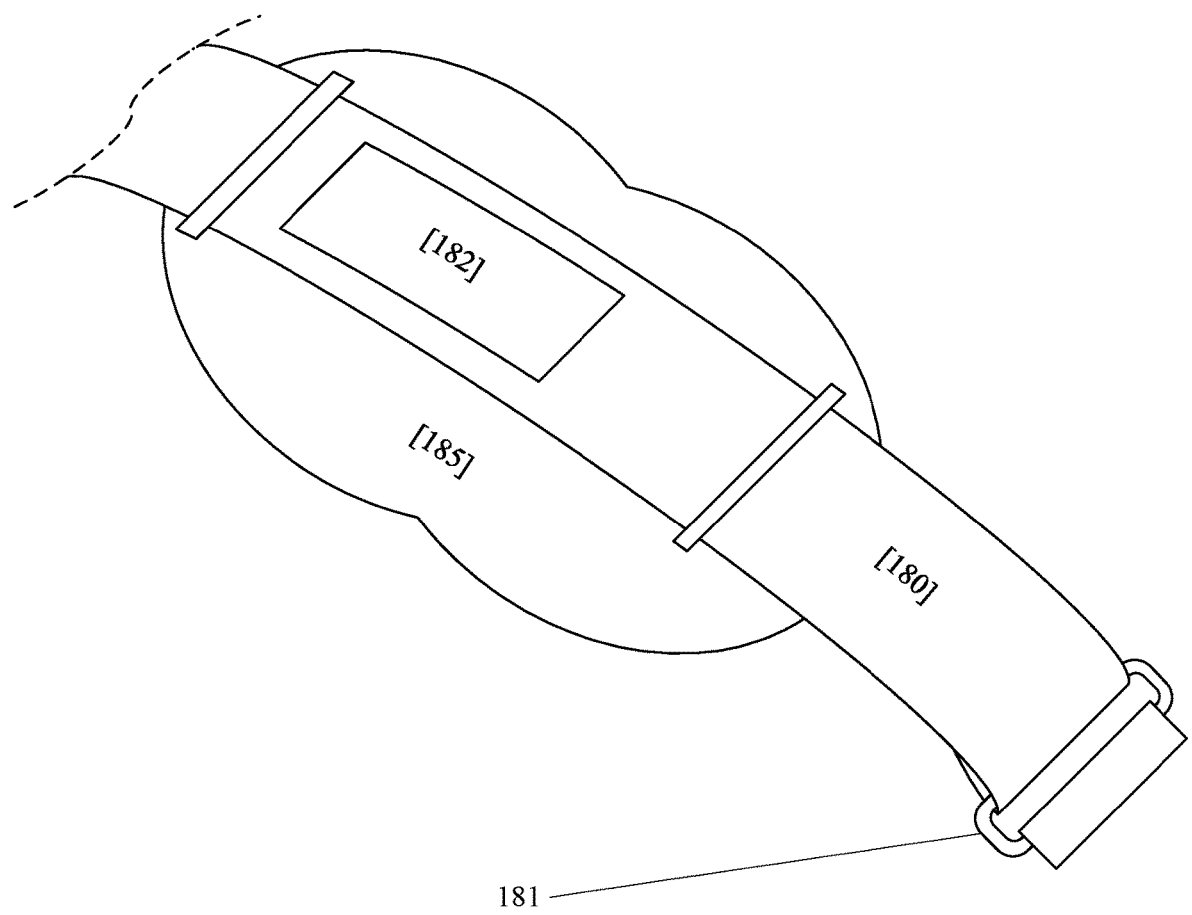
FIG. 5 is a line drawing of an eye mask for a whole-head pillow according to an exemplary embodiment of the invention.

FIG. 5 is a line drawing of an eye mask for a whole-head pillow according to an exemplary embodiment of the invention. As shown in FIG. 5, a strap 180 for a whole-head pillow can have an anchor point 181, a Velcro pad 182, and an eye mask 185. The strap 180 can be used to secure the left side of the whole-head pillow to the right side. The strap 180 can be used to tighten, fix, and retain the whole-head pillow to a user's head. The strap 180 can be preferably disposed on the whole-head pillow such that the strap 180 crosses a user's eyes. The strap 180 can have an eye mask 185 to provide comfort and block light from entering a user's eyes. The eye mask 185 can be slidably disposed on the strap 180. The eye mask 185 can provide padding and comfort and protect a user's face from the strap 180.

Figure 6:
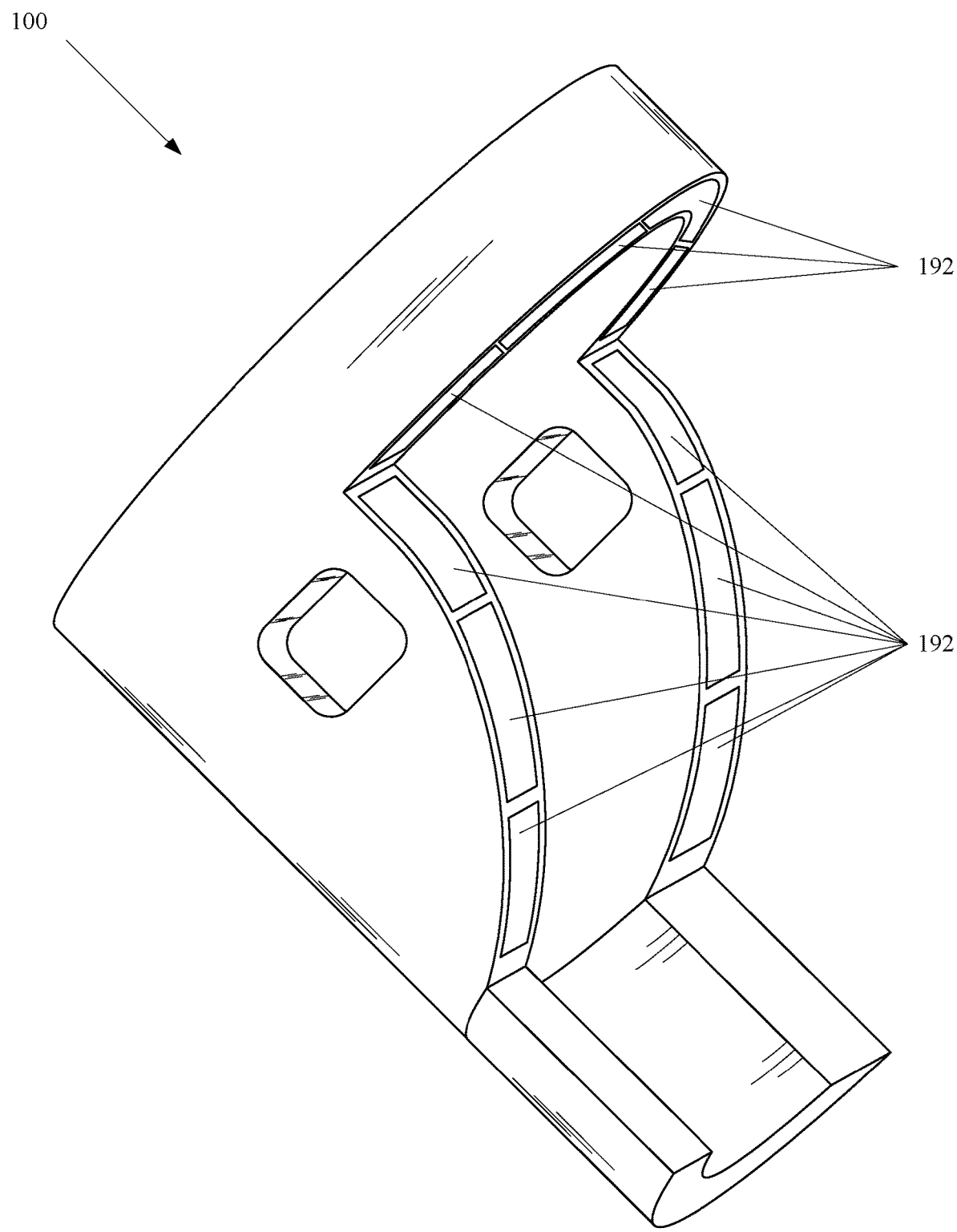
FIG. 6 is an isometric view of a right-side of a whole-head pillow according to an exemplary embodiment of the invention.
Figure 7:
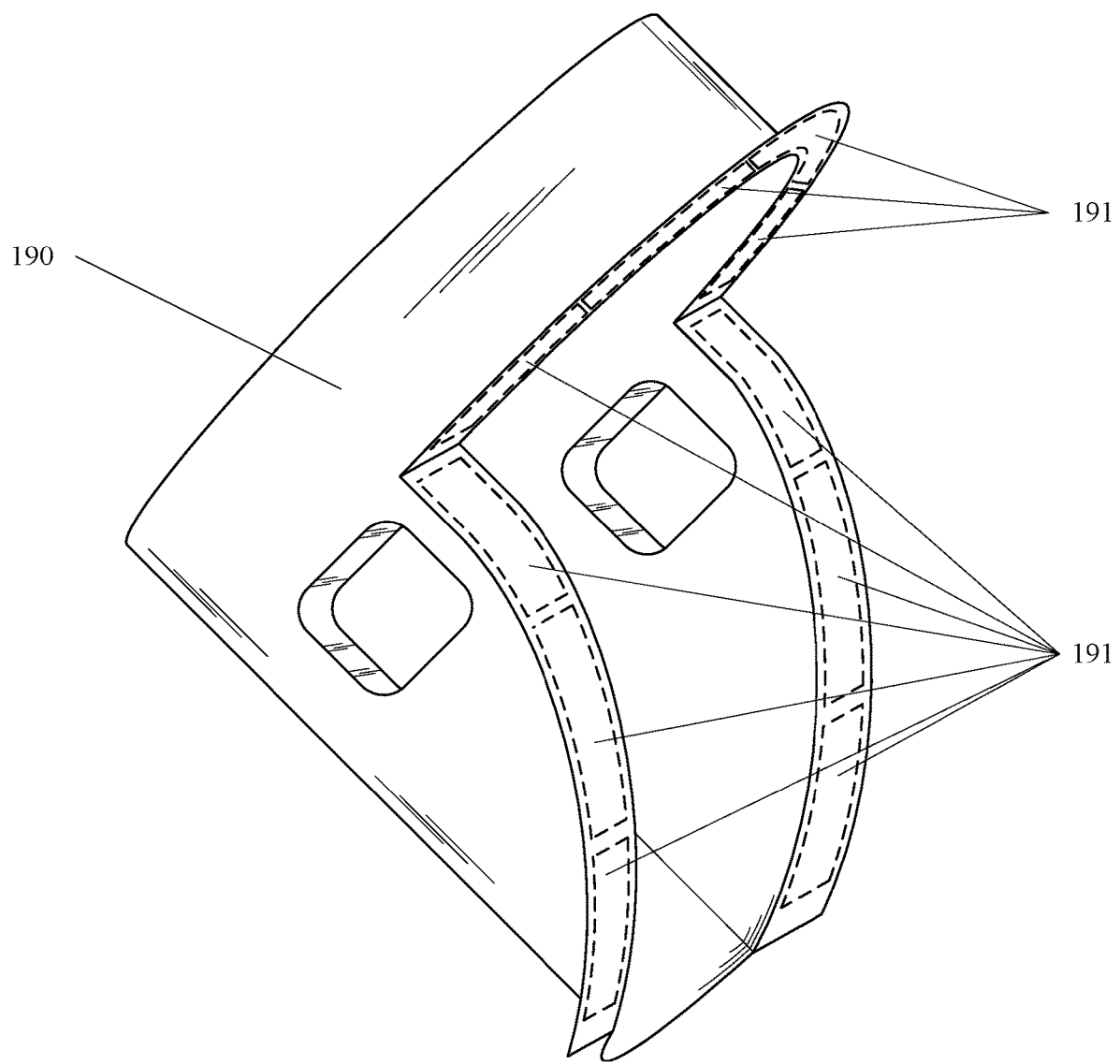
FIG. 7 is an isometric view of a right-side of a liner for a whole-head pillow according to an exemplary embodiment of the invention.

FIG. 6 is an isometric view of a right-side of a whole-head pillow according to an exemplary embodiment of the invention and FIG. 7 is an isometric view of a right-side of a liner for a whole-head pillow according to an exemplary embodiment of the invention. As shown in FIG. 6 and FIG. 7, a liner 190 can be sized in approximate proportion to be received in the whole-head pillow 100. A plurality of Velcro pads 192 around the open face of the whole-head pillow 100 can mate with corresponding Velcro pads 191 around a perimeter of the liner 190. The Velcro pads 191 and 192 can cooperate to retain the liner 190 in the whole-head pillow 100. Preferred embodiments of the invention include a liner 190. The liner 190 adds many benefits to the whole-head pillow 100 and can be removed from the whole-head pillow 100 for cleaning. Additionally, to the extent the liner 190 becomes worn, it can easily be replaced at minimal cost. The liner 190 can be made from a breathable natural fabric such as cotton. Cotton can be very comfortable against the skin and the liner 190 can cover interior portions of the whole-head pillow 100 that may have components (e.g. pads) that may be made from materials that are uncomfortable against the skin. The liner 190 can provide wicking to pull moisture and sweat away from a user's head.

Figure 8:
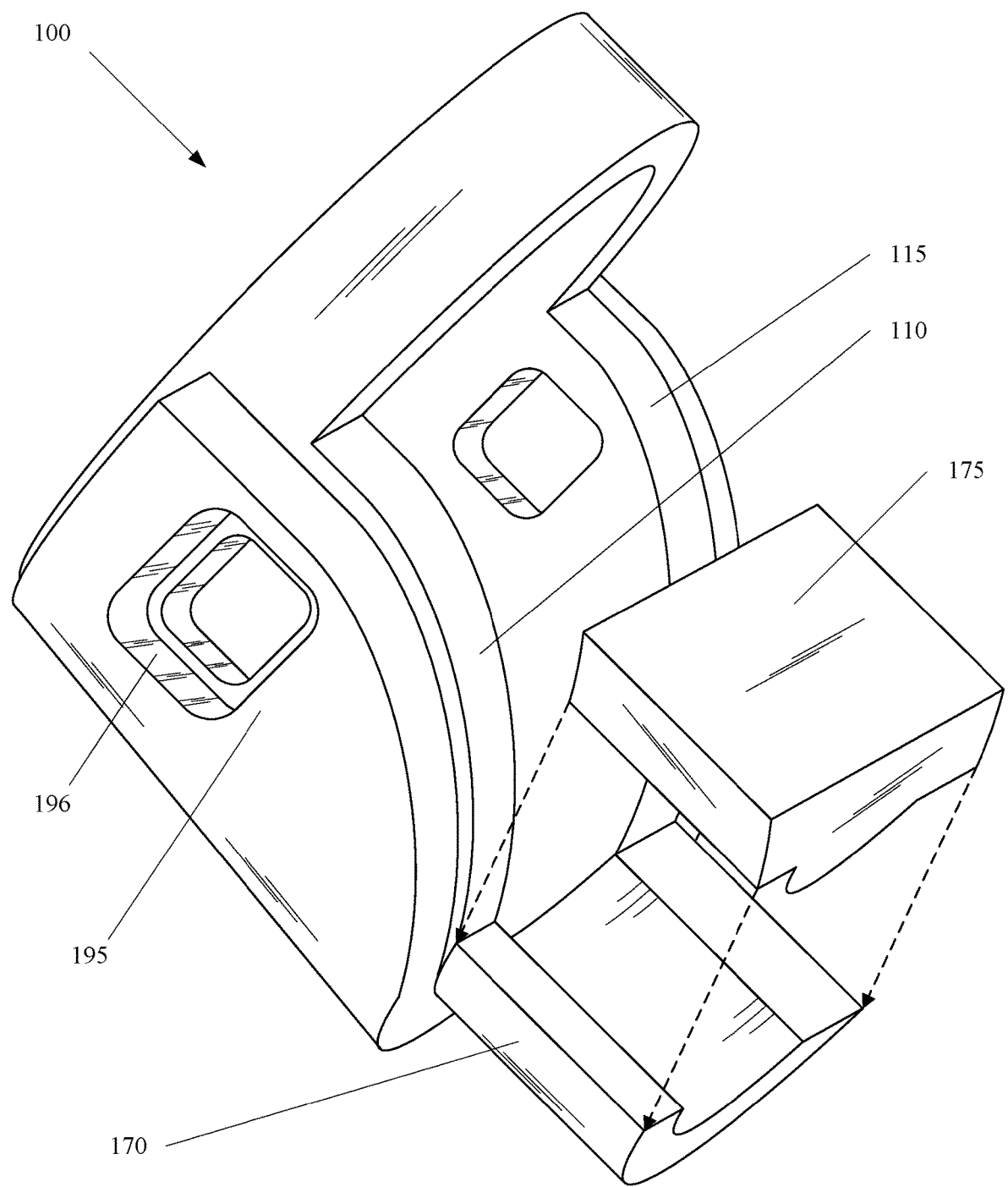
FIG. 8 is an isometric view of a right-side of a whole-head pillow and circumferential pad according to an exemplary embodiment of the invention.

FIG. 8 is an isometric view of a right-side of a whole-head pillow and circumferential pad according to an exemplary embodiment of the invention. As shown in FIG. 8, a whole-head pillow 100 can include a right side 110, a left side 115, a neck portion 170, a removable neck pillow 175, and a circumferential pillow 195 with earhole 196.

Some user's of a whole-head pillow 100 can be large humans having large shoulders and chests. Such large users may desire a whole-head pillow 100 that is proportionally larger than other user's may desire. For such users, embodiments of the whole-head pillow 100 include a circumferential pad 195 that can be wrapped around the outer surface of the whole-head pillow 100. The circumferential pad 195 can attach to the whole-head pillow 100 with Velcro (not shown). Commercial embodiments of the invention can come with multiple circumferential pads 195 of varying firmness and thickness to accommodate user preference. In one embodiment of the invention, the circumferential pad 195 can be inflatable so that a user can inflate the circumferential pad 195 to a desired thickness. The circumferential pad 195 can be formed from foam and have a cotton or synthetic cover. The circumferential pad 195 can have an earhole 196 disposed in an approximate location to correspond with an earhole (not labeled) in the whole-head pillow 100. The earhole 196 of the circumferential pad 195 can be slightly larger than an earhole (not labeled) in the whole-head pillow 100.

The neck portion 170 of the whole-head pillow can include a removable neck pad 175. Commercial embodiments of the invention can come with multiple neck pads 175 of varying firmness and thickness to accommodate user preference. In one embodiment of the invention, the neck pad 175 can be inflatable so that a user can inflate the neck pad 175 to a desired thickness. The neck pad 175 can be formed from foam and have a cotton or synthetic cover.

It will be apparent to those skilled in the art that various modifications and variations can be made in the whole-head pillow without departing from the spirit or scope of the invention. Thus, it is intended that embodiments of the invention cover the modifications and variations of this invention provided they come within the scope of the appended claims and their equivalents.

What is claimed is:

1. A pillow comprising:
   a head portion of the pillow, the head portion having a head-shaped cavity sized in approximate proportions to receive a human head, the head portion comprising:
      a fabric cover at least partially covering the head portion;
      an inner surface;
      an outer surface;
      an open face;
      a left side;
      a left-side ear hole;
      a right side;
      a right-side ear hole; and
      an open bottom;
   a plurality of removable sizing pads on the inner surface of the head-shaped cavity and disposed on top of the fabric cover, the plurality of removable sizing pads selectively removable from the head-shaped cavity to accommodate a variety of head sizes and configured for sizing the head-shaped cavity;
   a washable liner separate from the fabric cover and covering the plurality of removable sizing pads, the washable liner selectively removable from the pillow to accommodate laundering;
   a neck portion of the pillow, the neck portion extending from the open bottom; and
   a circumferential pad on the outer surface of the head portion; the circumferential pad selectively removable to increase or decrease the size of the head portion.

2. The pillow of claim 1 further comprising:
   a plurality of fasteners along a perimeter of the head-shaped cavity, the plurality of fasteners configured to retain the washable liner.

3. The pillow of claim 1 further comprising:
   a strap of the head portion of the pillow, the strap configured to retain a human head in the head-shaped cavity.

4. The pillow of claim 3 further comprising:
   an eye-mask of the strap, the eye-mask disposed in approximate location on the strap to cover a user's eyes.

5. The pillow of claim 1 further comprising:
   a top of the head portion, the top selectively removable.

6. The pillow of claim 1 further comprising:
   a neck pad of the neck portion, the neck pad selectively removable from the neck portion.

7. The pillow of claim 1 further comprising:
   an inside portion of the left-side ear hole on the inner surface of the head portion;
   an outside portion of the left-side ear hole on the outside surface of the head portion; and
   wherein the inside portion is larger than the outside portion.

8. A pillow selectively securable to a user's head, the pillow comprising:
   a head receiving portion, the head receiving portion sized in approximate proportions to receive a human head and comprising:
      a fabric cover at least partially covering the head receiving portion;
      a rear wall;
      a first sidewall;
      a first ear-hole in the first sidewall;
      a second sidewall;
      a second ear-hole in the second sidewall;
      an open front;
      an open bottom;
   a strap having a first end fixed to the first sidewall;
   a strap receiving portion fixed to the second sidewall, the strap receiving portion configured to receive the strap;
   a first removable sizing pad selectively attached to an inside surface of the head receiving portion and disposed on top of the fabric cover, the first removable sizing pad configured for sizing the head receiving portion in accordance with user preference; and
   a second removable sizing pad selectively attached to an outside surface of the head receiving portion configured for sizing the head receiving portion in accordance with user preference.

9. The pillow of claim 8 further comprising:
   a neck portion extending from the open bottom; and
   a third removable sizing pad selectively attached to the neck portion configured for sizing the neck portion in accordance with user preference.

10. The pillow of claim 8 further comprising:
   an eye-mask of the strap, the eye-mask disposed in approximate location on the strap to cover a user's eyes.

11. The pillow of claim 8 further comprising:
   an inside portion of the first ear hole on the inside surface of the head receiving portion;
   an outside portion of the first ear hole on the outside surface of the head receiving portion; and
   wherein the inside portion is larger than the outside portion.

12. The pillow of claim 8 further comprising:
   a washable liner covering at least the first pad, the washable liner selectively removable from the pillow to accommodate laundering.

13. The pillow of claim 8 further comprising:
   a plurality of fasteners along a perimeter of the head receiving portion, the plurality of fasteners configured to retain the washable liner.

14. The pillow of claim 8 wherein the second removable sizing pad is attached to at least the first sidewall and the second sidewall.

15. An orthopedic pillow to be secured to a user's head during sleep, the orthopedic pillow comprising:

a contoured socket for receiving the user's head, the contoured socket configured to substantially cover a back and sides of the user's head;

a front opening of the contoured socket;

a strap fixed to a first side of the front opening and configured to interface with an attachment point on a second side of the front opening, the strap and the attachment point configured to cooperate to secure the user's head in the contoured socket;

a fabric cover at least partially covering an inside surface of the contoured socket;

a first removable sizing pad removably attached to the inside surface of the contoured socket and disposed on top of the fabric cover, the first removable sizing pad configured to adjust the size of the contoured socket;

a second removable sizing pad removably attached to an outside surface of the contoured socket; and a removable liner separate from the fabric cover and covering at least part of the inside surface of the of the contoured socket.

16. The orthopedic pillow of claim 15 further comprising:
a removable top portion of the contoured socket.

17. The orthopedic pillow of claim 15 further comprising:
a first earhole in the contoured socket;
a second earhole in the contoured socket;
a third earhole in the removable liner corresponding to the first earhole; and
a fourth earhole in the removable liner corresponding to the second earhole.

18. The orthopedic pillow of claim 15 further comprising:
a first earhole in the contoured socket;
an inner perimeter of the first earhole;
an outer perimeter of the first earhole; and
wherein the inner perimeter is larger than the outer perimeter.

19. The orthopedic pillow of claim 15 further comprising:
an eye mask attached to the strap.

* * * * *